United States Patent [19]
Holtman

[11] 4,333,463
[45] Jun. 8, 1982

[54] ABSORBENT STRUCTURE CONTAINING SUPERABSORBENT

[75] Inventor: Dennis C. Holtman, Orland Park, Ill.

[73] Assignee: Johnson & Johnson Baby Products Company, New Brunswick, N.J.

[21] Appl. No.: 207,523

[22] Filed: Nov. 17, 1980

[51] Int. Cl.³ .............................................. A41B 13/02
[52] U.S. Cl. .................................. 128/287; 128/290 R
[58] Field of Search .................. 128/284, 287, 290 R, 128/296

[56] References Cited

U.S. PATENT DOCUMENTS

| | | | |
|---|---|---|---|
| 3,017,304 | 1/1962 | Burgeni | 128/290 R |
| 3,364,931 | 1/1968 | Hirsch | 128/290 R |
| 4,055,180 | 10/1977 | Karami | 128/284 |
| 4,103,062 | 7/1978 | Aberson et al. | 128/284 |

Primary Examiner—C. Fred Rosenbaum
Attorney, Agent, or Firm—Martha A. Michaels

[57] ABSTRACT

The present invention provides an absorbent structure for body fluids comprising a moisture-impermeable backing, an absorbent batt superimposed thereon and a moisture-permeable cover covering at least the side of the batt opposite the backing sheet. The absorbent batt contains a reservoir capable of receiving at least 75% of the discharge of body fluid in one second. The reservoir is located in the void zone, is formed by compression of the fibers and contains superabsorbent deposited therein.

11 Claims, 7 Drawing Figures

ABSORBENT STRUCTURE CONTAINING SUPERABSORBENT

BACKGROUND OF THE INVENTION

Disposable absorbent structures such as disposable diapers, sanitary napkins and incontinence pads have met with increased commercial acceptance in recent years primarily because of their convenience. Many different constructions have been proposed and used and some have met with wide-spread commercial success in spite of certain inadequacies in functional properties.

One of the most serious prior art problems has been the inability to provide a suitable construction that can accept a large void of body fluids. This is particularly true of the incontinent whether the incontinent be active and working or ill and bedridden. Various attempts have been made to provide special structures to absorb a large body fluid void. These include U.S. Pat. No. 3,441,024 to H. J. Ralph, U.S. Pat. No. 3,747,602 to H. J. Ralph, U.S. Pat. No. 3,968,798 to H. C. Hokanson and U.S. Pat. No. 4,067,366 to R. L. Johnson. While these various constructions were designed to assist the adult incontinent, the problem of providing an overall absorbent structure which will handle a full volume discharge of urine without leakage and retain the discharge still remains.

Whether the incontinent be an adult or infant, disposable structures generally have not accepted and held a full volume discharge of urine without leakage onto clothing. Similarly, the sanitary napkin shown in the art will not necessarily hold a full volume discharge of menstrual fluid. The present invention provides an absorbent structure which may be used as an infant diaper, an adult incontinence device, a sanitary napkin, an incontinence pad, or the like.

SUMMARY OF THE INVENTION

The present invention provides an absorbent structure to receive and contain body fluids comprising a loosely-compacted, cellulosic fibrous batt having a moisture-impermeable backing sheet on one side and a fabric cover which covers at least the side of the absorbent batt opposite the backing sheet on the other side. The absorbent batt is provided with a reservoir which has a capacity to hold at least 75% of the body fluid discharged in one second. The reservoir is situated in the void zone, is formed by compression of the cellulosic fibers in that zone, and contains a dry solid water-swellable, water-insoluble absorbent composition.

The absorbent structure may be incorporated in a disposable diaper such as for an infant or in an adult diaper with a larger liquid holding capacity. Furthermore, the absorbent structure may be incorporated in a sanitary napkin as well as in an incontinence pad. In each instance, the opening of the reservoir is placed in the void zone allowing immediate acceptance by the reservoir of the body fluid discharge. Generally the discharge capacity of the reservoir will be at least 10 cc.

The reservoir is created by compression of the loosely-compacted, cellulosic fibers in the reservoir area. The compaction may be carried out by application of pressure in the shape desired for the reservoir. This may be done by a stamping-type operation or by an embossing roll or the like.

DETAILED DESCRIPTION OF THE INVENTION

Figure 1:
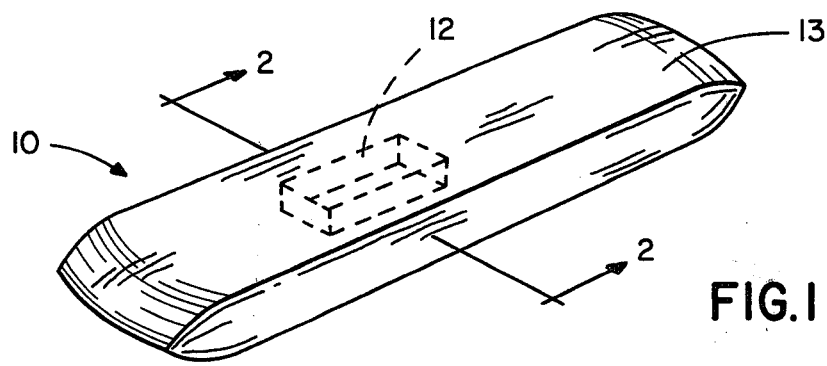
FIG. 1 is a perspective view of one embodiment of the present invention.

While this invention is susceptible of embodiment in many different forms, there is shown in the drawings, and herein will be described in detail, preferred embodiments of the invention and modifications thereof. It is understood that the present disclosure is to be considered as an exemplification of the principles of the invention and is not intended to limit the invention to the embodiments illustrated. The scope of the invention will be pointed out in the appended claims.

Figure 2:
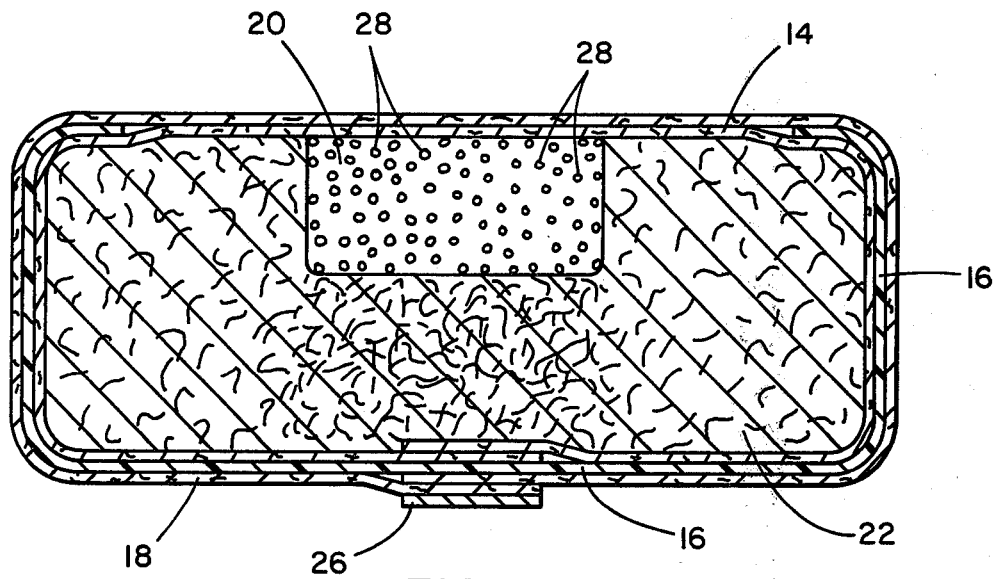
FIG. 2 is a cross-sectional view taken along line 2—2 of the embodiment of FIG. 1.

Referring to the drawings, and particularly to FIG. 1, an absorbent structure 10 is provided with a reservoir 12 lying below the cover 13. The cover is a moisture-permeable non-woven fabric. FIG. 2 shows the absorbent structure of FIG. 1 in cross-sectional view along line 2—2. The moisture-permeable exterior cover 18 completely wraps the absorbent structure. A moisture barrier 16 which is a moisture-impermeable backing sheet covers the bottom areas as well as both sides of the structure. Immediately adjacent the cellulosic batt 22 is a wrap of tissue 14. It may not be necessary to have a tissue wrapping the cellulosic batt, but if the cellulosic batt is quite thick, such as an inch or more, it may be desirable to provide a tissue wrap to assist with maintenance of the desired shape of the absorbent structure. The cellulosic fibrous batt 22 is provided with a reservoir 20 and a densified fibrous region 24. The reservoir 20 contains a water-swellable, water-insoluble absorbent composition 28. The surface of the fibrous batt containing the opening of the reservoir 20 is placed toward the wearer with the opening in the void zone. A release liner 26 is removed to expose adhesive so as to secure the structure to the underwear of the wearer.

Figure 3:
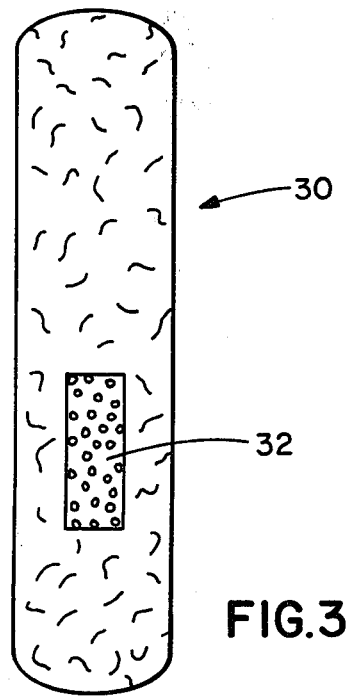
FIG. 3 is a top view of another embodiment of the present invention.
Figure 4:
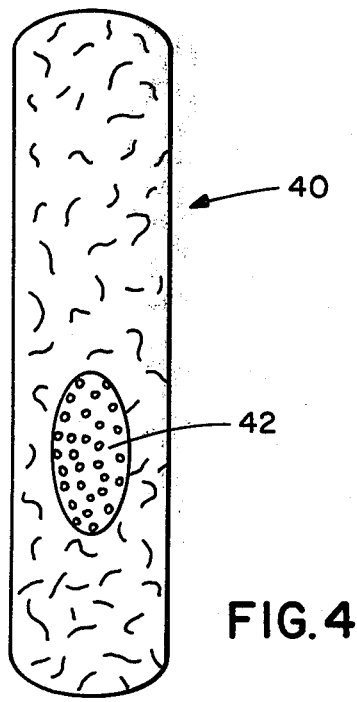
FIG. 4 is a top view of still another embodiment of the present invention.

FIGS. 3 and 4 are top views of typical cellulosic batts used in the absorbent structure of the invention. The cellulosic batt 30 contains a reservoir 32 having the shape of a rectangle. The reservoir may be located nearer one end of the cellulosic batt 30, e.g., one-third of the way or between the center and end to assist in location in the void zone of the wearer. In FIG. 4, a cellulosic batt 40 is provided with the reservoir 42 having an oval shape. Any desired shape and size may be used so long as the reservoir covers at least one square inch of surface and contains at least 10 cc in volume.

Figure 5:
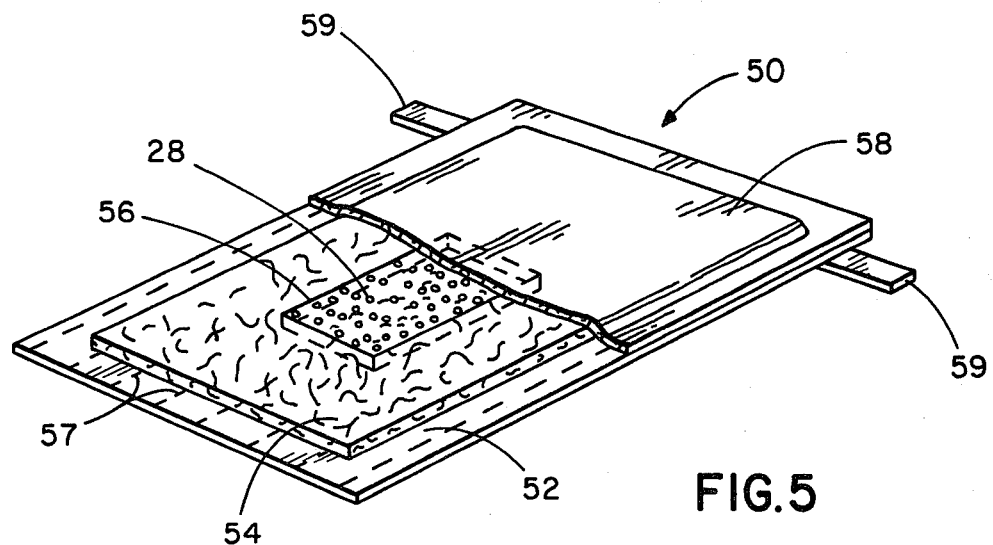
FIG. 5 is a perspective view of a disposable diaper utilizing the absorbent structure of the present invention.

Referring now to FIG. 5, a disposable diaper 50 is shown having a moisture-impermeable backing sheet 52. Super-imposed upon the backing sheet 52 is a loosely-compacted cellulosic fibrous batt 54. The fibrous batt contains a reservoir 56 created by compression or compaction of the fibers in that region. Within the reservoir are contained particles of a superabsorbent 28. The cellulosic batt 54 is covered by a moisture-permeable facing 58 of non-woven fabric. The facing and backing are adhered in the margin region. In addition glue lines 57 are used to secure the fibrous batt to the backing. Tape tabs 59 are provided to secure the diaper about the wearer.

Figure 6:
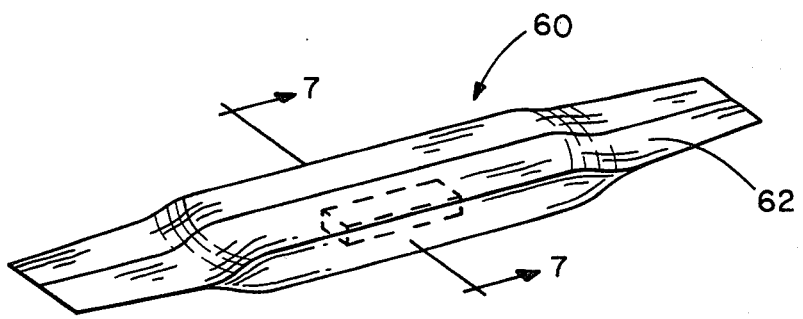
FIG. 6 is a perspective view of a sanitary napkin incorporating the absorbent structure of the present invention.
Figure 7:
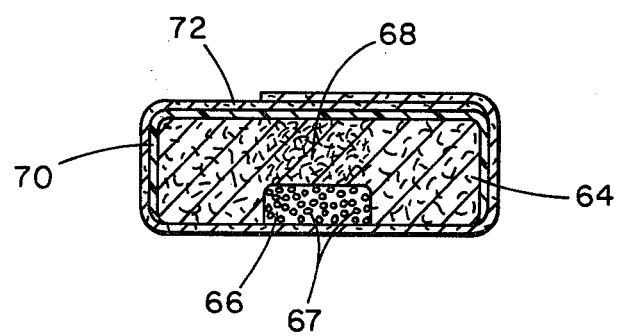
FIG. 7 is a cross-sectional view taken along line 7—7 of FIG. 6.

Referring now to FIGS. 6 and 7, a sanitary napkin 60 is depicted. The cover 62 shown in FIG. 6 is a moisture-permeable non-woven fabric. FIG. 7 is a cross-sectional view taken along lines 7—7 of FIG. 6. A cellulosic fibrous batt 64 is partially surrounded by a moisture barrier 70. The entire structure is wrapped in the moisture-permeable cover 72. The cellulosic batt 64 contains a reservoir 66. Within the reservoir 66 are superabsorbent particles 67. At the bottom of the reservoir is a dense fibrous area 68. The dense fibrous area 68 is created when the reservoir 66 is formed. The loosely-compacted, cellulosic fibrous batt used in the absorbent structure of the present invention is formed from wood pulp fibers, rayon fibers, or cotton linters, or mixtures thereof. The batt is primarily held together by interfiber bonds requiring no added adhesive. In some instances, the batt may contain synthetic fusible fibers, such as polyethylene, polypropylene and the like. The batt is a low bulk density coherent web of loosely-compacted, cellulosic fibers preferably comminuted wood pulp fibers in the form of so-called "fluff." The reservoir in the cellulosic batt is created by compressing the portion of the batt which it is desired to become a reservoir. The compression should be sufficient to create a reservoir, sufficient depth to hold at least 10 cc. The base of the reservoir is a densified fibrous region wherein the fibers are compacted. The densified region quickly absorbs the body fluid and commences distribution of the fluid to other parts of the cellulosic batt. In addition, it may be desirable to provide a paper-like densified layer on the side of the batt opposite the reservoir which receives the original discharge. The paper-like densified layer is formed by a slight moistening of the surface of the batt followed by light compaction using the application of pressure. U.S. Pat. No. 3,017,304, Burgeni, provides such a densified layer in a loosely-compacted, cellulosic fibrous batt.

The cover or facing provided on the absorbent structure of the present invention is a non-woven fabric having a high degree of moisture-permeability. For example, the fabric may be polyester, polyethylene, polypropylene, nylon, rayon or the like. Preferably the fabric used for the cover is a lightweight fabric in the range of 0.3–5.0 oz. per square yard and with a density less than 0.2 gms/cc. The most suitable fabrics have unusually high elongation, loft, softness and drape characteristics. Though the cover is moisture-permeable, it is preferably of the type which after permeation of the moisture, prevents strike-back of the body fluid when the absorbent structure is approaching saturation.

The body of the cellulosic fibrous batt is substantially more wettable than the cover and tends to draw liquid away from the facing layer. Thus the void occurs and the cover is permeated and the liquid deposited in the reservoir. The individual fibers of the batt are extremely wettable and thus draw the liquid into the fibrous batt. The base of the reservoir is a densified fibrous region wherein the capillary radius is quite small. Thus the capillary pressure is increased and the liquid is rapidly distributed to portions of the cellulosic batt. The densified fibrous region at the base of the reservoir provides the maximum capillary pressure because it combines the very low contact angle of the fibers of the batt with the high density of the densified fibers.

The individual fibers of the batt are extremely wettable, generally having liquid-fiber contact angles below about 15° and approaching zero in the optimum embodiment. The wickability or preferential absorptivity of the body of the batt for water is limited, however, by its low density which results in large effective capillary radius for the capillaries between adjacent fibers.

Thus when urine is voided into an area in the cover layer, it partially wets a small portion of the cover layer and is passed through the cover layer almost instantaneously to the first reservoir. In the first reservoir, the liquid comes into contact with the body of the batt and the densified region surrounding the reservoir. It is preferentially absorbed into the densified region because of its small capillary structure and then into the body of the batt because of the enhanced wettability of the walls of the reservoir. The body fluid then passes through the densified region and into the second reservoir whereupon the superabsorbent particles begin their absorption of the liquid. The absorbent structure performs in the same manner whether the body fluid is urine, a menstrual fluid, or other liquid exudate.

The superabsorbent particles are generally a dry solid water-swellable, water-insoluble absorbent composition such as an ionic complex of a water-soluble anionic polyelectrolyte and a polyvalent metal cation. Typical super-absorbent compositions are illustrated in U.S. Pat. No. 4,090,013 to S. H. Ganslaw et al and U.S. Pat. No. 4,043,952 to S. H. Ganslaw et al. The superabsorbent may be in the form of individual particles or strips of film to which superabsorbent is adhered to other known superabsorbent compositions. The superabsorbent may be affixed to the base of the superabsorbent reservoir or may simply lie independently within the reservoir.

It will be understood by those skilled in the art that variations and modifications of the specific embodiments described above may be employed without departing from the spirit and scope of the invention as defined in the appended claims.

The pressure causing a liquid to enter a cylindrical capillary is expressed by the equation $$P = (2v \cos \theta / r)$$

wherein
P is the capillary pressure,
$v$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and increases with narrower capillary radii so that narrower capillaries will draw liquid from wider ones.

The relative wickability between the cover layer and the body of the fibrous batt is affected by both the relative densities of the layers and the relative wettability of the individual fibers in each layer. The individual fibers of the batt have substantially smaller liquid-fiber contact angles than those of the cover layer overcoming the density difference and providing a substantial overall increase in capillary pressure to absorb liquid into the body of the batt.

A densified fiber layer such as that at the base of the reservoir provides the maximum capillary pressure because it combines the very low contact angle of the fibers of the batt with the high density (small capillary radius) of the densified fibers.

I claim:

1. An absorbent structure suitable for absorption of body fluids comprising a moisture-impermeable backing sheet; an absorbent, loosely-compacted cellulosic fibrous batt, superimposed on said backing sheet; and a moisture-permeable fabric cover, covering at least the side of said absorbent batt opposite said backing sheet, said absorbent batt being provided with a reservoir having a capacity sufficient to hold at least 75% of the body fluid discharged in one second and containing deposited therein a water-swellable, water-insoluble absorbent composition, said reservoir being situated in the void zone and being formed by the compression of the cellulosic fibrous batt.

2. The absorbent structure of claim 1 wherein the reservoir is created by a depression in the fibrous batt and has a capacity of at least 10 cc.

3. The absorbent structure of claim 1 wherein the base of the reservoir is a densified region of the fibers of the fibrous batt.

4. The absorbent structure of claim 1 wherein the reservoir is located between the center and one transverse end of the absorbent structure.

5. The absorbent structure of claim 1 wherein the capacity of the reservoir is sufficient to hold at least 90% of the body fluid discharged in one second.

6. An adult incontinence device substantially rectangular in shape comprising a moisture-impermeable backing sheet; an absorbent, loosely-compacted cellulosic fibrous batt superimposed on said backing sheet; and a moisture-permeable fabric cover, covering at least the side of said absorbent batt opposite said backing sheet, said absorbent batt being provided with a reservoir covering at least one square inch of the surface of the batt and having a capacity of at least 10 cc and containing deposited therein a water-swellable, water-insoluble absorbent composition, said reservoir being situated in the void zone and being formed by compression of the cellulosic fibrous batt.

7. The adult incontinence device of claim 6 wherein said backing sheet is provided with an adhesive strip for securement of the device when worn.

8. A disposable diaper comprising a moisture-impermeable backing sheet; an absorbent, loosely-compacted cellulosic fibrous batt, superimposed on said backing sheet; and a moisture-permeable facing superimposed on the side of the fibrous batt opposite said backing sheet, said absorbent batt being provided with a reservoir having capacity sufficient to hold at least 75% of the body fluid discharged in one second and contained deposited therein a water-swellable, water-insoluble absorbent composition, acid reservoir being situated in the void zone and being formed by compression of the cellulosic fibrous batt.

9. The disposable diaper of claim 8 wherein the reservoir has as its base a densified region and has a capacity of at least 10 cc.

10. A sanitary napkin containing a moisture-permeable outer layer containing an absorbent, loosely-compacted cellulosic fibrous batt, said absorbent batt being provided with a reservoir having a capacity sufficient to hold at least 75% of the body fluid discharged in one second and containing deposited therein a water-swellable, water-insoluble absorbent composition, said reservoir being situated in the void zone and being formed by compression of the cellulosic fibrous batt.

11. The sanitary napkin of claim 10 wherein the base of the reservoir is a densified region of the fibers of the fibrous batt.

* * * * *